(12) United States Patent
Kim et al.

(10) Patent No.: US 12,014,537 B2
(45) Date of Patent: Jun. 18, 2024

(54) ORGAN CLASSIFICATION SYSTEM AND METHOD

(71) Applicant: INTROMEDIC CO., LTD., Seoul (KR)

(72) Inventors: You Jin Kim, Muan-gun (KR); Du Hyun Choi, Seoul (KR); Young Dae Seo, Sejong (KR)

(73) Assignee: INTROMEDIC CO., LTD., Seoul (KR)

( * ) Notice: Subject to any disclaimer, the term of this patent is extended or adjusted under 35 U.S.C. 154(b) by 122 days.

(21) Appl. No.: 17/615,457

(22) PCT Filed: Dec. 10, 2020

(86) PCT No.: PCT/KR2020/018086
§ 371 (c)(1),
(2) Date: Nov. 30, 2021

(87) PCT Pub. No.: WO2021/141252
PCT Pub. Date: Jul. 15, 2021

(65) Prior Publication Data
US 2022/0230415 A1 Jul. 21, 2022

(30) Foreign Application Priority Data
Jan. 10, 2020 (KR) .................. 10-2020-0003794

(51) Int. Cl.
G06K 9/00 (2022.01)
A61B 5/00 (2006.01)
G06V 10/764 (2022.01)

(52) U.S. Cl.
CPC .......... *G06V 10/764* (2022.01); *A61B 5/7264* (2013.01); *A61B 2576/02* (2013.01); *G06V 2201/03* (2022.01)

(58) Field of Classification Search
CPC ... A61B 1/041; A61B 1/0005; A61B 1/00009; A61B 1/000094; A61B 1/045;
(Continued)

(56) References Cited

U.S. PATENT DOCUMENTS

2007/0248254 A1 10/2007 Mysore et al.
2009/0023993 A1* 1/2009 Davidson ............. A61B 1/0005
382/128
(Continued)

FOREIGN PATENT DOCUMENTS

KR 100802839 B1 2/2008
KR 100946203 B1 3/2010
(Continued)

OTHER PUBLICATIONS

International Search Report dated Mar. 16, 2021 for PCT application No. PCT/KR2020/018086.

*Primary Examiner* — Alex Kok S Liew

(57) ABSTRACT

The present invention relates to an organ classification system, and the system for classifying the type of an organ may comprise: a search unit for searching an input image for a frame where an image regarding an organ starts, on the basis of a plurality of organ images pre-learned according to types of organs; an obtainment unit for obtaining an image of a found frame from the input image; and a storage unit for storing location information of the found frame in the input image.

11 Claims, 7 Drawing Sheets

(58) Field of Classification Search
CPC ............ A61B 1/00036; A61B 1/00055; A61B 1/00016; A61B 1/00045; A61B 1/00147; A61B 1/005; A61B 5/1128; A61B 1/000096; A61B 5/073; A61B 5/14539; G06T 7/0012; G06T 2207/10068; G06T 2207/10016; G06T 2207/20081; G06T 2207/30028; G06T 2207/30092; G06T 2207/20084; G06T 2207/30004; G06T 7/70; G06T 2207/10028; G06T 5/003; G06T 2207/30096; G06T 7/0016; G06T 7/11; G16H 30/40; G16H 50/20; G16H 30/20; G16H 20/40

See application file for complete search history.

(56) References Cited

U.S. PATENT DOCUMENTS

| | | | | |
|---|---|---|---|---|
| 2011/0075902 | A1* | 3/2011 | Song | G06T 7/66 |
| | | | | 382/128 |
| 2011/0301447 | A1* | 12/2011 | Park | G06T 7/0016 |
| | | | | 600/407 |

FOREIGN PATENT DOCUMENTS

| | | | |
|---|---|---|---|
| KR | 20190046530 A | 5/2019 | |
| KR | 102037303 B1 | 10/2019 | |

* cited by examiner

ORGAN CLASSIFICATION SYSTEM AND METHOD

TECHNICAL FIELD

The disclosure relates to a system and method for classifying organs, and more particularly to an organ classification system and method which learn organ images based on deep learning to classify organ images.

BACKGROUND ART

An internal-organ image or a digestive-organ image refers to an image which is obtained by capturing the inside of a human body and needed for a specialist to diagnose problems with organs. Such an organ image is a necessary image for diagnosing a patient's body condition, and includes many images of esophagus, stomach, small intestine, large intestine, etc.

A landmark refers to a thing or feature which is generally used as a target suitable for distinguishing a certain location. In a medical field, such a landmark is marked on a specific area of the organ image and used for identifying the type of organ.

Conventionally, a specialist used to read a clinical case in person and manually mark a landmark of a digestive organ. However, such manual marking has problems that a specialist has to do a lot of work and it takes long time.

Accordingly, there is a need of a system that receives an organ image in real time, automatically identifies the organ image, and classifies organs.

DISCLOSURE

Technical Problem

The disclosure is conceived to solve the foregoing conventional problems, and an aspect of the disclosure is to previously learn images about organs through deep learning, searching for a frame, in which an image of an organ starts to appear, in an input image, and showing a user the found frame.

Technical Solution

To achieve the aspect of the disclosure, there is provided an organ classification system including: a searcher configured to search for a frame, in which an image corresponding to an organ starts to appear, in an input image based on a plurality of organ images previously learned according to types of organs; an acquirer configured to acquire an image of the found frame in the input image; and a storage configured to store location information about the found frame in the input image.

Here, the searcher may be configured to use a binary search method to search for the frame, in which the image corresponding to the organ starts to appear, in the input image.

Further, the searcher may be configured to perform a binary search with regard to the input image based on the binary search method, identify whether the found organ image is further upstream or downstream than a target organ image, and continue the binary search for searching for the frame, in which the target organ image starts to appear, in an upstream or downstream direction.

Further, the input image may include a first organ image, a second organ image, a third organ image and a fourth organ image; the first organ image may correspond to esophagus, the second organ image may correspond to stomach, the third organ image may correspond to small intestine, and the fourth organ image may correspond to large intestine; and the first organ image, the second organ image, the third organ image and the fourth organ image may be input in sequence from the first organ image to the fourth organ image.

In addition, in a case where the searcher searches for a frame, in which the second organ image starts to appear, based on the binary search method, the binary search may be continued when the found organ image is identified as the second organ image, the third organ image or the fourth organ image after the binary search is first performed with regard to the input image; and the binary search may be terminated and sequential searching may be performed when the found organ image is identified as the first organ image.

Further, in a case where the searcher searches for a frame, in which the third organ image starts to appear, based on the binary search method, the binary search may be continued when the found organ image is identified as the third organ image or the fourth organ image after the binary search is first performed with regard to the input image; and the binary search may be terminated and sequential searching may be performed when the found organ image is identified as the first organ image or the second organ image.

Further, the organ classification system may further include a landmark display configured to display a landmark corresponding to the frame, in which the image corresponding to the organ starts to appear, based on location information about the found frame, in the input image.

Further, the organ classification system may further include a time-bar generator configured to generate a time bar based on information about display of the landmark and display the time bar on a user interface.

In addition, the time bar may represent esophagus, stomach, small intestine and large intestine in sequence.

Further, the time-bar generator may be configured to display the time bar with a plurality of sections, of which lengths are relatively varied depending on the number of frames in images corresponding to esophagus, stomach, small intestine and large intestine.

Further, an image corresponding to an organ may be displayed on the user interface when a user moves an input unit to the landmark.

In addition, the time-bar generator may be configured to generate the time bar in which esophagus, stomach, small intestine and large intestine are represented with different colors.

To achieve the aspect of the disclosure, there is provided an organ classification method including: by a searcher, searching for a frame, in which an image corresponding to an organ starts to appear, in an input image based on a plurality of organ images previously learned according to types of organs; by an acquirer, acquiring an image of the found frame in the input image; and by a storage, storing location information about the found frame in the input image.

Advantageous Effects

An organ classification system and method according to the disclosure have effects as follows.

First, it is possible to provide convenience. In the organ classification system and method according to the disclosure, the organ classification system may previously learn the organ images classified into the plurality of organs. Based on the learned organ images, the organ images input in real time are classified according to the organs, and the time bar of the organ image is generated and provided to a specialist, thereby providing convenience in reading a clinical case.

Second, it is possible to save time. In the organ classification system and method according to the disclosure, the organ classification system may previously learn the organ images classified into the plurality of organs, and use the binary search technique to raise the searching speed of the organ images in the future. Therefore, it is possible to save time in classifying the organ images acquired in real time.

MODE FOR CARRYING OUT DISCLOSURE

Below, embodiments of the disclosure will be described with reference to the accompanying drawings. Although some features unrelated to the gist of the disclosure will be omitted or abstracted, the omitted features are not useless in the disclosure but may be used as combined by a person having ordinary knowledge in the art to which the disclosure pertains.

Figure 1:
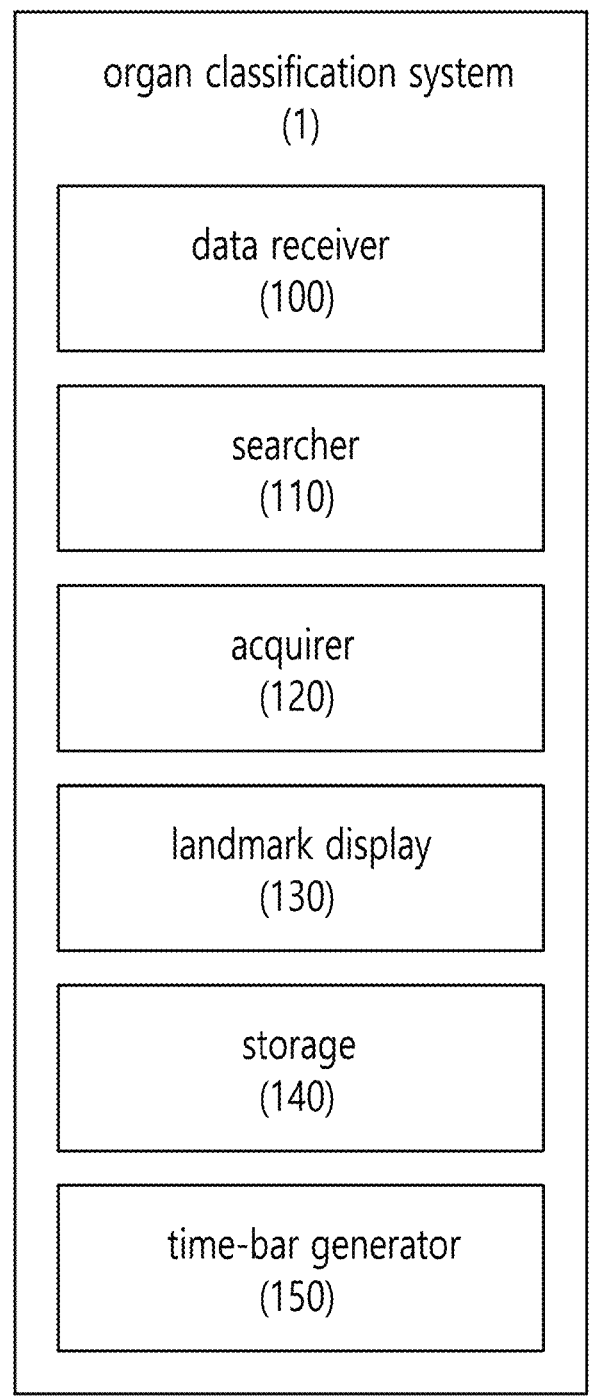
FIG. 1 is a block diagram of an organ classification system according to an embodiment of the disclosure.

FIG. 1 is a block diagram of an organ classification system 1 according to an embodiment of the disclosure.

As shown in FIG. 1, the organ classification system 1 according to an embodiment of the disclosure may include a data receiver 100, a searcher 110, an acquirer 120, a landmark display 130, a storage 140, and a time-bar generator 150. Such an organ classification system 1 may be provided in a capsule endoscope and used as software for supporting capsule-endoscopic diagnosis.

In terms of diagnosing a lesion in digestive organs by capturing an image of internal organs, in particular, digestive organs of a human body, there have been used various examination methods such as an ultrasonic examination, a tomography examination, etc. However, an endoscopy method, by which a diagnostic expert makes a diagnosis while seeing the inside of the digestive organ with his/her own eyes, has been preferred because its diagnostic accuracy is high.

In particular, capsule endoscopy is not only easy to conduct a medical examination but also less unacceptable and less painful for an examinee. Further, the capsule endoscopy makes it possible to diagnose a lesion in small intestine that is generally difficult to reach. Thus, the use of the capsule endoscope is gradually increasing. The capsule endoscope is swallowed by a patient through a mouth, and captures images while sequentially cruising esophagus, stomach, small intestine and large intestine inside a human body. The captured images are transmitted to an external receiver through radio frequency (RF) communication, human body communication, and the like wireless communication method. Therefore, the organ classification system 1 according to the disclosure may be provided in the capsule endoscope and transmit information obtained by classifying organs to a specialist or a user.

The data receiver 100 is configured to receive a plurality of organ images from a specialist. The data receiver 100 may be connected to a specialist's terminal through a wired/wireless network and receive information about the plurality of organ images. A specialist may classify the plurality of organ images into digestive organs of esophagus, stomach, small intestine and large intestine. Here, the plurality of organ images may include tens of thousands of images. Further, the data receiver 100 may be configured to receive an image, which is obtained by capturing an internal organ of a human body of a patient or an examinee through the capsule endoscope and transmitted in real time, i.e., an input image. The input image is captured by the capsule endoscope inside a human body in real time and transmitted to a user interface or a display which is visible to a user's naked eyes. Because the capsule endoscope travels inside a human body of a patient or an examinee starting from esophagus, the input images may be transmitted in order of esophagus, stomach, small intestine and large intestine.

The searcher 110 is configured to learn the plurality of organ images corresponding to esophagus, stomach, small intestine, large intestine, etc. classified by a specialist, and search for a frame, in which an image corresponding to an organ starts to appear, in the input image based on a result of learning the plurality of organ images. The searcher 110 may use a binary search technique to search for a frame, in which an image corresponding to an organ starts to appear, in the input image.

Here, the searcher 110 may learn the organ images of esophagus, stomach, small intestine, large intestine, etc. based on deep learning. A deep-learning model used by the searcher 110 may be based on combination of a convolutional neural network (CNN) model and fully convolutional network (FCN) model. Here, the FCN is used for predicting which class the pixels of the organ image belong to. In other words, the FCN is used to semantically segment objects in an image.

For example, esophagus, stomach, small intestine and large intestine individually have their own characteristic shapes, and such shapes may be shown in organ images of distinctive shapes such as presence of projections like the lining of stomach, presence of villi like the lining of small intestine, other wrinkled lining, etc. Based on such shapes, the searcher 110 may learn the plurality of organ images received from a specialist and identify images of esophagus, stomach, small intestine and large intestine in the input images.

The acquirer 120 is configured to capture and acquire the image of the frame found by the searcher 110 in the input image received from the capsule endoscope in real time.

The landmark display 130 is configured to display a landmark 170 at a location, where an organ starting frame is present, on the time bar based on location information of the frame found by the searcher 110. Here, the location information refers to information about what organ image is acquired in successive input images in which esophagus, stomach, small intestine and large intestine are captured in real time, so that the landmark display 130 can identify information about a frame where an image corresponding to an organ starts to appear in the input image.

The storage 140 is configured to store location information about a found frame in an input image. Further, the storage 140 may be configured to store the plurality of organ images received from a specialist as sorted according to the organs, details that the searcher 110 has searched for the frames where the images corresponding to the organs start to appear, etc. The details may include date and time on which the input image is input, date and time on which the searcher 110 searches for the input image, etc.

The time-bar generator 150 is configured to generate a time bar based on information about the time bar marked with the landmark 170 and display the generated time bar on a user interface or a display. The time-bar generator 150 may generate the time bar in which esophagus, stomach, small intestine and large intestine are displayed in sequence. In addition, the time-bar generator 150 may generate the time bar to be displayed on the user interface by segmenting the time bar into a plurality of sections having relative lengths based on ratios among the actual lengths of esophagus, stomach, small intestine and large intestine. Further, the time-bar generator may represent sections corresponding to esophagus, stomach, small intestine and large intestine with different colors on the time bar. Here, the user interface or the display may for example employ a MiroView program.

Below, an organ classification method will be described with reference to the accompanying drawings.

Figure 2:
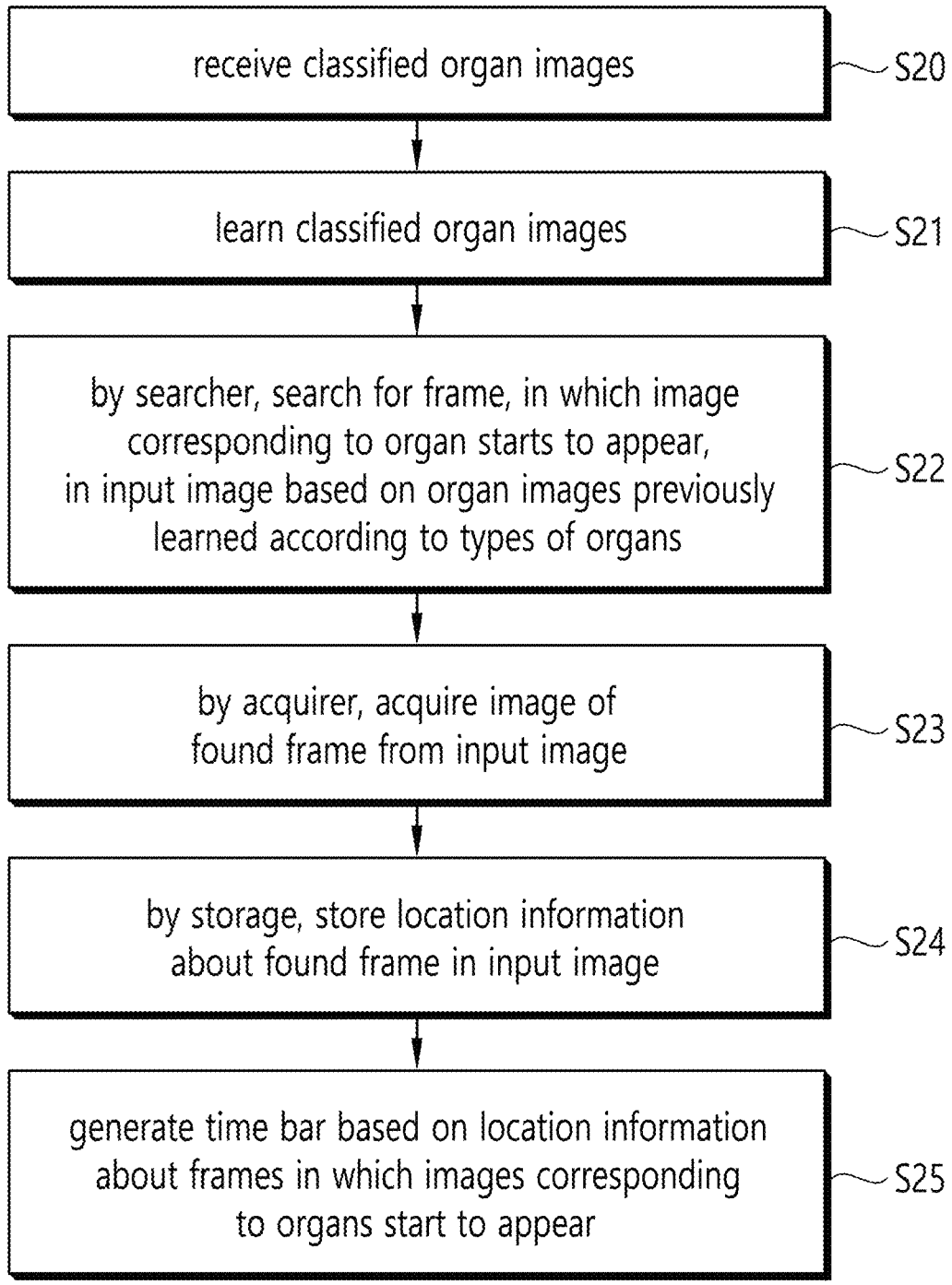
FIG. 2 is a flowchart of an organ classification method according to an embodiment of the disclosure.

FIG. 2 is a flowchart of the organ classification method according to an embodiment of the disclosure.

As shown in FIG. 2, the organ classification method according to an embodiment of the disclosure first receives a plurality of organ images of which classification has already been completed. <S20> In this regard, the plurality of organ images of which the classification has already been completed will be described with reference to FIG. 3.

Figure 3:
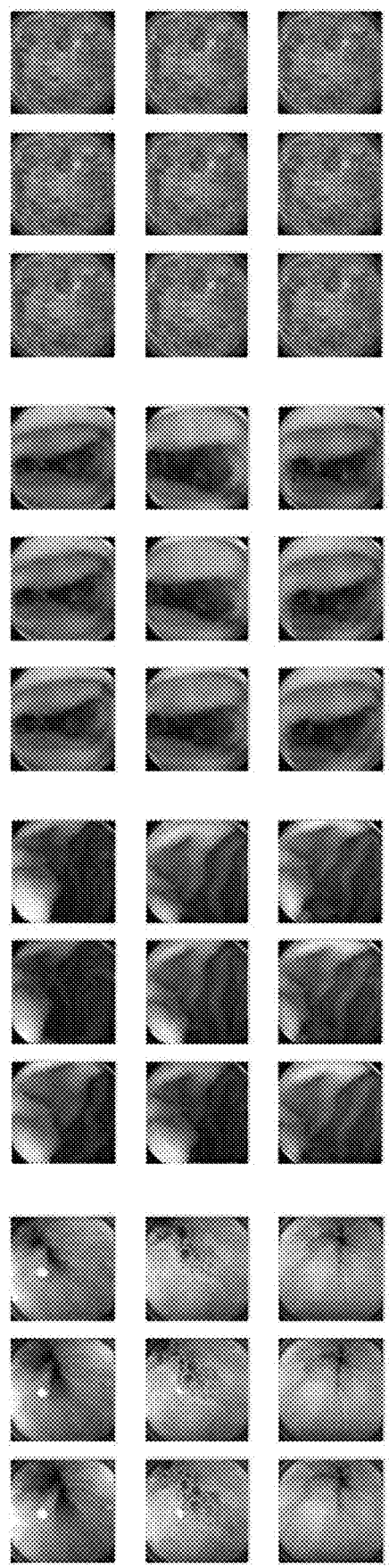
FIG. 3 shows examples of images which are classified by organs by a specialist in the organ classification system according to an embodiment of the disclosure.

FIG. 3 shows examples of images which are classified by organs by a specialist in the organ classification system 1 according to an embodiment of the disclosure.

As shown in FIG. 3, the plurality of classified organ images may include a plurality of organ images classified by a specialist according to esophagus, stomach, small intestine, large intestine, etc. Because the same type of organ may differ in shape from person to person, the same part of the organ is variously included in the plurality of classified organ images and classified into the organ image corresponding to the same type of organ, thereby dividing cases of various organ images.

Therefore, the organ images may be classified into esophagus in such a manner that various organ images obtained by capturing specific parts of esophagus are grouped into the same organ image. Further, an image of esophagus including a foreign material may also be classified into the same organ image of esophagus.

In addition, the organ images may be classified into stomach in such a manner that various organ images obtained by capturing specific parts of stomach are grouped into the same organ image. Further, an image of stomach including a foreign material may also be classified into the same organ image of stomach.

Likewise, the organ images may be classified into small intestine in such a manner that various organ images obtained by capturing specific parts of small intestine are grouped into the same organ image. Further, an image of small intestine including a foreign material may also be classified into the same organ image of small intestine.

Further, the organ images may be classified into large intestine in such a manner that various organ images obtained by capturing specific parts of large intestine are grouped into the same organ image. Further, an image of large intestine including a foreign material may also be classified into the same organ image of large intestine.

Although FIG. 3 illustrates that nine organ images are classified into each of esophagus, stomach, small intestine and large intestine, it is merely an example. Therefore, a lot of same organ images more than nine organ images may be grouped.

Next, the plurality of classified organ images is learned. <S21>

The plurality of organ images classified by an expert may be stored in the storage 140 of the organ classification system 1. The storage 140 may be provided inside or outside the organ classification system 1. When the storage 140 is provided outside the organ classification system 1, the organ classification system 1 can access data of the storage 140 through communication. Therefore, the plurality of classified organ images may be learned by the searcher 110 with reference to the storage 140. In this case, the searcher 110 may use the deep learning model to learn the organ images of each of esophagus, stomach, small intestine, large intestine, etc.

Here, the deep learning model may employ the CNN model as a basic model, and additionally use the FCN model for segmenting objects in the organ image into sematic units.

In general, the CNN model refers to an artificial neural network that consists of input and output layers as well as multiple hidden layers and uses a convolutional operation. The hidden layer of the CNN model generally includes a series of convolutional layers related to multiplication or other inner products. An activation function is commonly a rectified linear unit (ReLU), and is followed by additional convolutions such as pooling layers, fully connected layers, and normalization layers, which are called hidden layers because inputs and outputs are masked by the activation function and final convolution.

The CNN model may be used in classifying images and trained by a back propagation algorithm because it has a structure suitable for learning two-dimensional (2D) data and is one of representative models widely used in various application fields such as object classification, object search, etc. in an image. Thus, the searcher 110 according to the disclosure can classify and learn the plurality of organ images through the CNN model. The CNN model is publicly known, and thus detailed descriptions thereof will be omitted.

In addition, the FCN model provided at the final layer of the CNN model has a network structure for semantically segmenting objects from a plurality of organ images as described above. In other words, the FCN model is to predict which class the pixels of the organ image belong to, through classification.

Here, the classification refers to technology for identifying whether a specific target is present in the image. The FCN model typically has a structure where the pooling layer is added to a multistage convolution layer, and a fully connected layer is generally provided in a posterior portion of the network. Therefore, all information related to a location or a space is lost after an image goes through the fully connected layer.

Here, convolution in the convolutional layer refers to a process of connecting neurons and areas while passing through filters. Because one or more feature maps are needed to recognize an image, the convolutional layer has multiple feature maps. Therefore, the pooling layer following the convolutional layer forms a feature map with compressed features to output a characteristic part on an image.

Further, detection technology does not only identify whether a specific object is present, but involves location information unlike the classification. Commonly, the detection involves location information about an object based on a quadrangular area called a bounding box. Therefore, the detection is divided into an operation of identifying the class and an operation of obtaining the location information. The semantic segmentation does not simply show an object desired to be detected through the bounding box, but separates an object in semantic units by performing prediction in units of pixels. The semantic unit refers to a target desired to be learned by a neural network on an image. For example, when a dog is learned from a picture of a dog and a cat, the dog is regarded as the semantic unit, and the technology of distinguishing between the dog and the cat in units of pixels is the semantic segmentation.

The semantic segmentation needs to identify not only what object is present in an image but also where the object is located. However, the semantics and the location are fundamentally different in aiming, and therefore required to be harmonized for improving the performance of the semantic segmentation. Such harmonization may be achieved by the FCN.

In the FCN model, the network for classification uses the fully connected layer in its posterior portion, and there is a problem that the fully connected layer receives an input of only a fixed size. Further, there is a problem that the location information is lost after going through the fully connected layer. Therefore, if the fully connected layer is regarded as a 1×1 convolutional operation, the location information is not lost but left. Accordingly, the input image is not restricted.

Further, a certain map is decreased in size after going through multistage convolutional layers and pooling layers. Therefore, to make prediction in units of pixels, a process of increasing the result of the decreased certain map is needed. In this case, bilinear interpolation may be used as the simplest method of enlarging the result of the certain map. However, from the point of view of learning that connects one end to the other end, it is necessary to decide through learning rather than using a fixed value. Therefore, an operation for removing the convolution, i.e., deconvolution is used, and a coefficient of a filter using the deconvolution is determined based on the learning. Accordingly, it is possible to learn the bilinear filter, and carry out nonlinear upsampling (or resolution restoration). However, it is difficult to expect performance higher than a certain level when the upsampling is simply performed. Thus, a skip layer is used in the FCN to improve the performance.

The basic concept of the skip layer is to reinforce a detailed part based on a result of a map ahead of the final map because the lost detailed part increases as a certain map becomes smaller while going through multistage convolutional layers and pooling layers. Therefore, it is possible to more accurately predict a certain map. The FCN model is publicly known, and thus detailed descriptions thereof will be omitted.

According to the disclosure, such general CNN and FCN models are used to learn the plurality of organ images. An overall process of learning the organ images by the organ classification system 1 through the CNN model and FCN model will be described with reference to FIG. 4.

Figure 4:
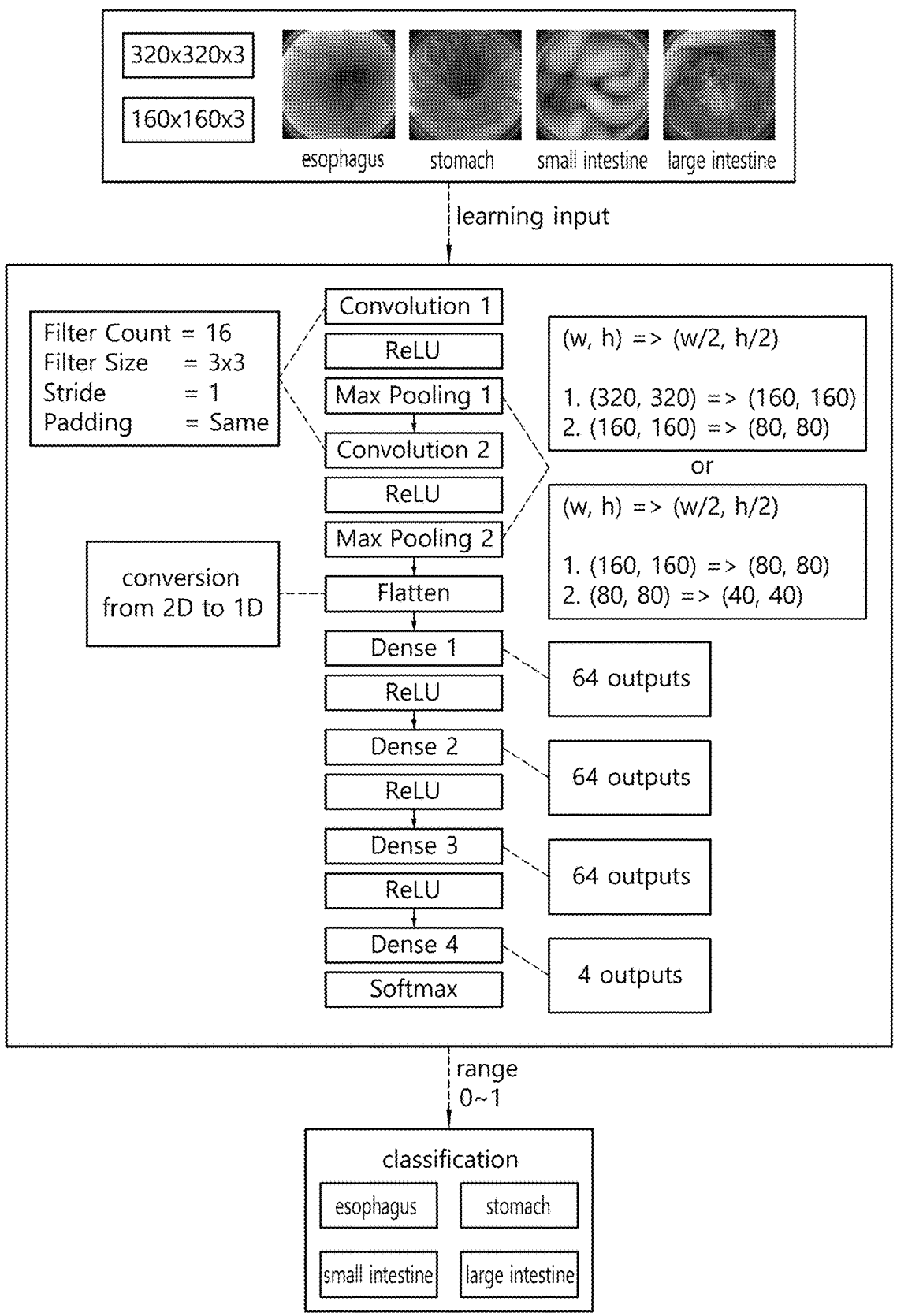
FIG. 4 shows a schematic process of learning organ images in the organ classification system according to an embodiment of the disclosure.

FIG. 4 shows a schematic process of learning organ images in the organ classification system 1 according to an embodiment of the disclosure.

As shown in FIG. 4, the searcher 110 may learn a plurality of organ images based on input data of organ images classified by an expert into esophagus, stomach, small intestine, large intestine, etc. In this case, the size of the organ image may be set to '320×320×3' or '160×160×3'. Therefore, the searcher 110 proceeds with convolution1 by applying the CNN model to the input organ images, and carries out max pooling by going through the ReLU layer. In this case, the convolution1 has a filter count of '16', a filter size of '3×3', a stride of '1', and padding of 'same'. Further, in the max pooling, the width and height of the organ image are decreased by half. In other words, (320, 320) may be decreased into (160, 160), and (160, 160) may be decreased into (80, 80).

After proceeding with the convolution1), the convolution2 may be performed. Even the convolution2 has a filter count of '16', a filter size of '3×3', a stride of '1', and padding of 'same'. Further, in the max pooling, the width and height of the organ image are decreased by half. In other words, (160, 160) may be decreased into (80, 80), and (80, 80) may be decreased into (40, 40).

Then, the outputs of the organ mage are reduced into 64 outputs while going through dense1 and ReLU, dense2 and ReLU, and dense3 and ReLU after converting the 2D organ image into one dimension, and then finally reduced into 4 outputs through dense4) and Softmax, thereby searching for the organ images corresponding to esophagus, stomach, small intestine and large intestine. Through this process, the searcher 110 can learn the plurality of organ images based on the input data.

Next, the searcher 110 searches for a frame, in which an image corresponding to an organ starts to appear, in the input image based on the plurality of organ images previously learned according to the types of organs. <S22>

To search for a frame in which an image corresponding to an organ starts to appear, the searcher 110 may employ the binary search technique. In this regard, descriptions will be made with reference to FIG. 5.

Figure 5:
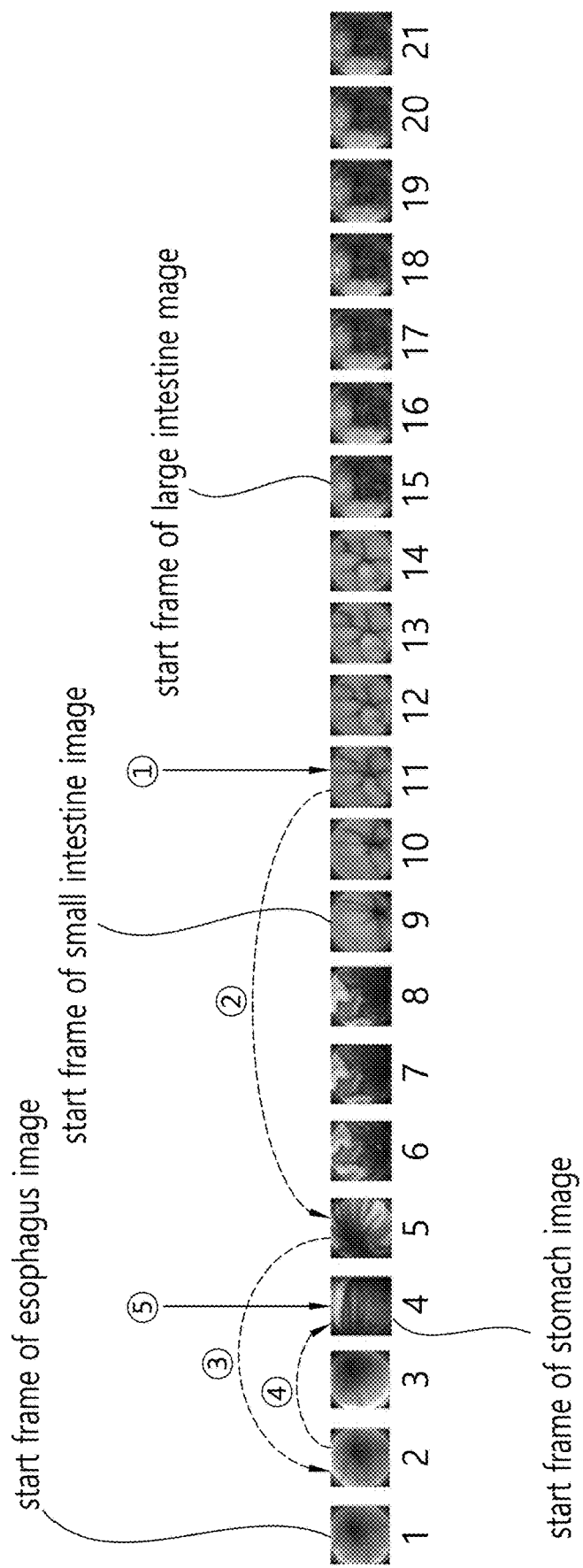
FIG. 5 schematically illustrates that a searching speed for an input image is increased by a binary search in the organ classification system according to an embodiment of the disclosure.

FIG. 5 schematically illustrates that a searching speed for an input image is increased by the binary search technique in the organ classification system according to an embodiment of the disclosure.

As shown in FIG. 5, it is optimized by the binary search technique that the searcher 110 searches for a start frame in a series of organ images and performs prediction.

Here, the binary search refers to a method of searching by dividing a set of sorted data into two parts. In other words, 'binary' means 'two different parts', and the binary search refers to a method in which the input data is divided in half and compared with a value desired by a user and only the part approximate to the desired value is divided in half again and subjected to searching.

For example, the binary search method of searching for a book No. 91 in a bookshelf will be described on the assumption that the books are arranged on the bookshelf in order of [12 16 20 28 33 46 52 64 68 71 83 88 91 96 99].

Specifically, the book No. 64 in the middle is first identified, and the books at the right side are second selected because No. 91 is higher than No. 64. The book No. 88 in the middle is third identified among the books at the right side, and the books at the right side are fourth selected again because No. 91 is higher than No. 88. The book No. 96 in the middle is fifth identified among the books at the right side, and the book at the left side is sixth identified because No. 91 is lower than No. 96, thereby finally finding the book No. 91.

In such a manner, the searcher 110 may use the binary search technique to search for a frame in which an image corresponding to an organ starts to appear. Here, the frame refers to one of successive images or pictures corresponding to esophagus, stomach, small intestine and large intestine in the input image. For example, it will be described as shown in FIG. 5 that the searcher 110 searches for a frame in which an image corresponding to stomach starts to appear.

In FIG. 5, a total of 21 input images corresponding to organs, in other words, the first to third frames corresponding to esophagus, the fourth to eighth frames corresponding to stomach, the ninth to fourteenth frames corresponding to small intestine, and the fifteenth to twenty-first frames corresponding to large intestine are received as the input image. In this case, the input images are generally received in order of esophagus, stomach, small intestine and large intestine. This is because the capsule endoscope travels starting from esophagus inside a human body of a patient or a person to be examined, and thus the input images are transmitted in order of esophagus, stomach, small intestine and large intestine.

In addition, esophagus among esophagus, stomach, small intestine and large intestine is placed at a relatively upper side in the human body, and thus an upstream direction is represented toward esophagus. On the other hand, large intestine among esophagus, stomach, small intestine and large intestine is placed at a relatively lower side in the human body, and thus a downstream direction is represented toward large intestine.

For example, esophagus is located further upstream than stomach, small intestine and large intestine, stomach is located further upstream than small intestine and large intestine, and small intestine is located further upstream than large intestine. On the other hand, large intestine is located further downstream than esophagus, stomach and small intestine, small intestine is located further downstream than esophagus and stomach, and stomach is located further downstream than esophagus.

In this state, the searcher 110 may search for frames, in which images corresponding to organs start to appear, by the binary search technique.

Specifically, the eleventh frame in the middle may be first found among a total of 21 frames of the input image. In this case, the eleventh frame corresponds to small intestine among the found organ images of the input image. Here, the found organ images refer to the organ images resulting from searching the input image by the searcher 110. Because the eleventh frame corresponds to not stomach but small intestine, the searching is performed again to search for the frame in which the image corresponding to stomach starts to appear.

Here, the eleventh frame corresponds to small intestine, and small intestine is located further in the right direction than stomach. Therefore, the searcher 110 may perform searching in the left direction rather than the right direction to search for stomach. In other words, according to the disclosure, the searcher 110 previously knows that the input images are received in order of esophagus, stomach, small intestine and large intestine, and the input image received earlier is displayed on the user interface or the display at a leftward side because the input image corresponding to stomach is received earlier than the input image corresponding to small intestine with respect to time series order.

Alternatively, the input image received earlier based on the time series order may be displayed at a rightward side. In this way, the time series order is expressed according to embodiments.

Then, the searcher 110 may search for the fifth frame in the middle between the leftmost first frame and the eleventh frame. In this case, the fifth frame corresponds to stomach, but the searcher 110 does not know whether the fifth frame is the frame in which the image corresponding to stomach starts to appear. Therefore, the binary search technique is continued to search for the frame in which the image corresponding to stomach starts to appear.

Then, the searcher 110 may search for the second frame in the middle between the fifth frame and the leftmost first frame. In this case, the second frame corresponds to esophagus, and the searcher 110 identifies that the frame in which the image corresponding to stomach starts to appear has passed, and performs the binary search at the rightward side to search for the fourth frame in the middle between the second frame and the fifth frame. Because the searcher 110 can identify the time series order of the organs as described above, the searcher 110 performs the searching at the rightward side to search for the organ following esophagus, in other words, stomach.

Last, when the searcher 110 searches again for the third frame in the middle between the second frame and the fourth frame at the left side to identify the frame in which the organ image corresponding to stomach starts to appear, the fourth frame is set as the frame in which the image corresponding to stomach starts to appear because the third frame corresponds to esophagus. Likewise, the start frames corresponding to esophagus, small intestine and large intestine may also be found by the same method.

In this way, the searcher 110 according to the disclosure may search the remaining frames through the binary search regardless of the number of input images until an image corresponding to a target organ, i.e., a frame in which a target organ image starts to appear is found. Therefore, the binary search technique according to the disclosure searches for a frame, in which an image corresponding to an organ starts to appear, in the input image regardless of the number of input images, thereby efficiently raising the speed of searching for a frame, in which an image corresponding to an organ starts to appear, in the input image.

According to the disclosure, the binary search technique may be performed in combination with sequential searching.

Specifically, the searcher 110 according to the disclosure uses the binary search technique to search for a frame, in which an image corresponding to an organ starts to appear, in the input image. However, it may be a little inefficient that the binary search is continuously performed to search for a frame, in which an image corresponding to esophagus or stomach starts to appear. In other words, stomach is actually shorter than small intestine or large intestine, and therefore the number of images corresponding to esophagus or stomach is significantly smaller than the number of images corresponding to small intestine or large intestine. Therefore, when the searcher 110 searches for a frame, in which an image corresponding to stomach starts to appear, it may be inefficient that the binary search is continued. Accordingly, it will be described with reference to FIG. 5 that the binary search technique is performed in combination with the sequential searching.

Specifically, as described above, the searcher 110 may first search for the eleventh frame in the middle among a total of 21 frames. In this case, the eleventh frame corresponds to not stomach but small intestine, and thus the searching is required to be performed again.

Here, the eleventh frame corresponds to small intestine, and small intestine is located further in the rightward direction than stomach, the searcher 110 may proceed with the searching in the leftward direction to search for stomach. Therefore, the searcher 110 may search for the fifth frame in the middle between the leftmost first frame and the eleventh frame. In this case, the fifth frame corresponds to stomach, but the searcher 110 does not know whether the fifth frame is the frame in which the image corresponding to stomach starts to appear. Therefore, the binary search technique is continued to search for the frame in which the image corresponding to stomach starts to appear.

Then, the searcher 110 may search for the second frame in the middle between the fifth frame and the leftmost first frame. In this case, the second frame corresponds to esophagus. In the foregoing embodiment, the binary search is performed again. However, in this embodiment, the searching is performed in sequence starting from the image corresponding to esophagus in order to search for the frame in which the image corresponding to stomach starts to appear. Because the number of images corresponding to esophagus is relatively small, it may be rather inefficient that the binary search is continuously performed.

Accordingly, both the binary search and the sequential searching are used to search for a frame in which an image corresponding to esophagus or stomach starts to appear, so that the searcher 110 can efficiently search for frames in which images corresponding to organs start to appear.

Further, if an image corresponding to esophagus or stomach is first found even when the searcher 110 searches for a frame in which an image corresponding to small intestine starts to appear, it may be inefficient to continuously perform the binary search.

Specifically, as described above, the number of images corresponding to esophagus or stomach may be significantly smaller than the number of images corresponding to small intestine or large intestine because esophagus or stomach is actually shorter than small intestine or large intestine. Therefore, if the binary search is continued when the searcher 110 searches for a frame, in which an image corresponding to small intestine starts to appear, it may be inefficient to use only the binary search because relatively many images corresponding to small intestine or large intestine may be searched once again at the second searching or the images corresponding to small intestine or large intestine may be likely to be searched again later.

Therefore, the searcher 110 according to the disclosure may initially use the binary search to search for even a frame in which an image corresponding to small intestine starts to appear, use both the binary search and the sequential searching to search images corresponding to esophagus or stomach, and continue the binary search when the image corresponding to small intestine or large intestine is found, thereby efficiently searching for the frame in which the image corresponding to small intestine starts to appear.

Next, the acquirer 120 acquires an image of a found frame from the input image. <S23>

The acquirer 120 may capture and acquire only start frames from images corresponding to organs found in the input image by the searcher 110, or may capture and acquire the whole input images. Such organ images acquired by the acquirer 120 may be stored in the storage 140.

In addition, the storage 140 is configured to store location information about the found frame in the input image.

<S24>

Specifically, the storage 140 is configured to store the location information about the frames in which the images corresponding to the organs start to appear in the whole input image, thereby storing which frame is a frame in which an image corresponding to esophagus starts to appear, which frame is a frame in which an image corresponding to stomach starts to appear, which frame is a frame in which an image corresponding to small intestine starts to appear, and which frame is a frame in which an image corresponding to large intestine starts to appear.

Last, a time bar 160 is generated based on the location information about the frames in which the images corresponding to organs start to appear. <S25>

The location information about the found frames is transmitted to the landmark display 130 so that the landmark display 130 can mark the frames, in which the images corresponding to the organs start to appear, with the landmark 170, and the time-bar generator 150 generates the time bar 160 based on the marking information about the landmark 170 so that the time bar 160 can be displayed on the user interface or the display. In this regard, descriptions will be made with reference to FIG. 6.

Figure 6:
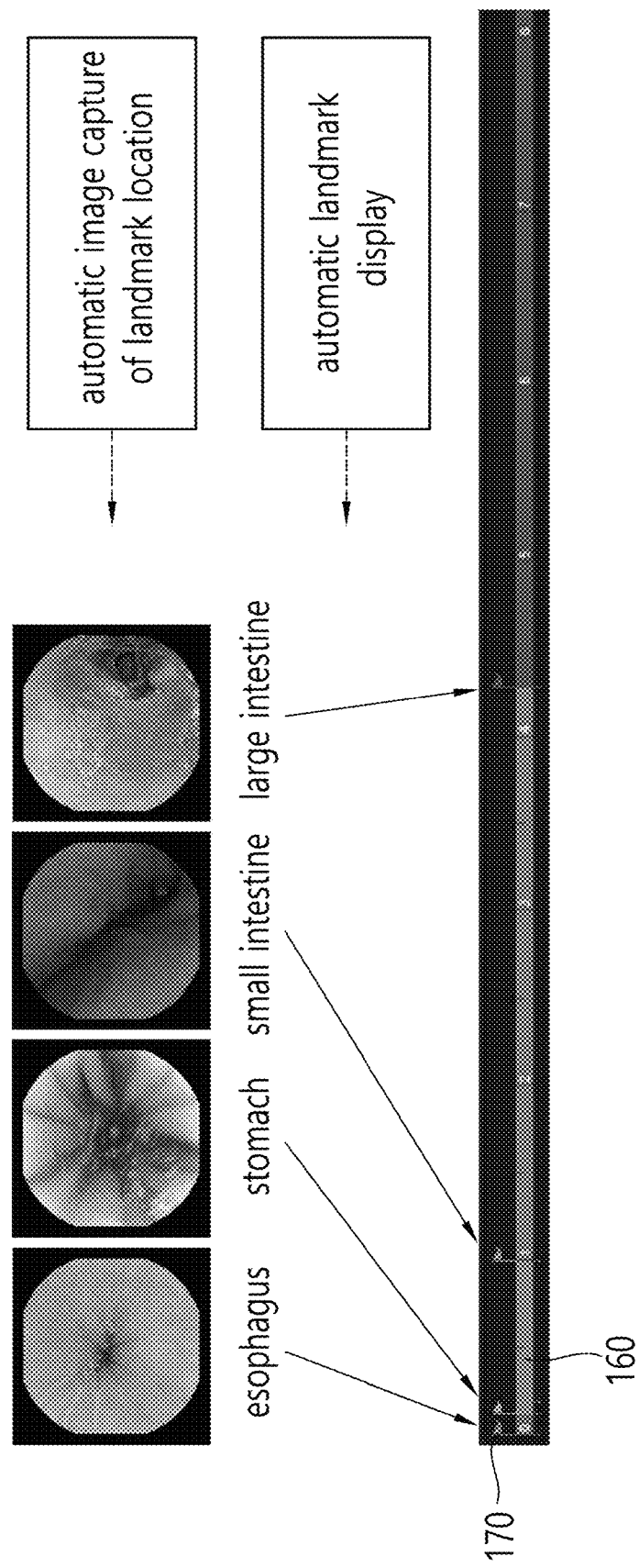
FIG. 6 illustrates that a time bar is generated and locations of frames where images of organs start to appear are marked in the organ classification system according to an embodiment of the disclosure.

FIG. 6 illustrates that the time bar 160 is generated and locations of frames in which images corresponding to organs start to appear are marked in the organ classification system according to an embodiment of the disclosure.

As shown in FIG. 6, the time bar 160 for the input image may be displayed on the user interface or the display. In other words, the time bar 160 is sectioned according to organs to represent the relative lengths of the organs, and is marked with the landmarks 170 at parts where frames, in which the images corresponding to the organs start to appear, are located to distinguish the sections of the organs. In this case, the organ images acquired by the acquirer 120 and marked with the landmarks 170 may be enlarged and shown to a user. The organ image may be popped up when a user moves a mouse cursor or the like input unit to the time bar 160 on the user interface or the display, may be popped up in response to a separate input, or may always be popped up without any separate input.

Here, the length of the organ sections shown on the time bar 160 are relatively represented in proportion to the number of frames corresponding to esophagus, stomach, small intestine and large intestine, thereby showing the length proportions of the organ sections. This is for representation for each individual person because the organ passing speed may differ from person to person.

Specifically, the length proportions of esophagus, stomach, small intestine and large intestine are as follows: in general, esophagus of 35 cm, stomach of 40 cm, small intestine of 7 m, and large intestine of 1.5 m in a total length of 9.25 m. However, the capsule endoscope stays fora long time in large intestine. In other words, the capsule endoscope relatively quickly passes esophagus or stomach, but small intestine is so long that long time is taken for the capsule endoscope to pass small intestine. Although large intestine is shorter than small intestine, the capsule endoscope stays long in large intestine. Therefore, the number of frames corresponding to esophagus and stomach is less than the number of frames corresponding to small intestine or large intestine, and therefore the length proportions of the organs are relatively represented on the time bar 160 based on the number of frames corresponding to the organ images. In this way, according to the disclosure, the time-bar generator 150 generates the time bar 160 based on the number of frames corresponding to the organs, and thus gives more detailed information about the organs to a user or a specialist.

Further, the sections corresponding to the organs on the time bar 160 may be represented with different colors so that a user can easily distinguish between the organs.

In addition, frames, in which images corresponding to organs such as esophagus, stomach, small intestine and large intestine start to appear in sequence, may be marked with different landmarks 170, and the different landmarks 170 make it easier to display the organ images on the user interface or the display.

Here, the different landmarks 170 may refer to the landmarks 170 marked on the time bar 160 and different in shape. For example, the landmark 170 for classification of esophagus may have a triangular shape, the landmark 170 for classification of stomach may have a quadrangular shape, the landmark 170 for classification of small intestine may have a circular shape, and the landmark 170 for classification of large intestine may have a stellate shape. Such shapes of the landmark 170 are different according to different organ images, thereby making it easier to classify the organ images.

In addition, the different landmarks 170 may refer to the landmarks 170 different in color from one another. For example, the landmark 170 for classification of esophagus may have red color, the landmark 170 for classification of stomach may have blue color, the landmark 170 for classification of small intestine may have a green color, and the landmark 170 for classification of large intestine may have yellow color. The shapes of the landmark 170 are different according to different organ images, thereby making it easier to classify the organ images.

Meanwhile, the time bar 160 displayed on the user interface or the display according to the disclosure may show a user an approximate location of the capsule endoscope based on the function of the landmark 170 for the classification of the organs. In this regard, descriptions will be made with reference to FIG. 7.

Figure 7:
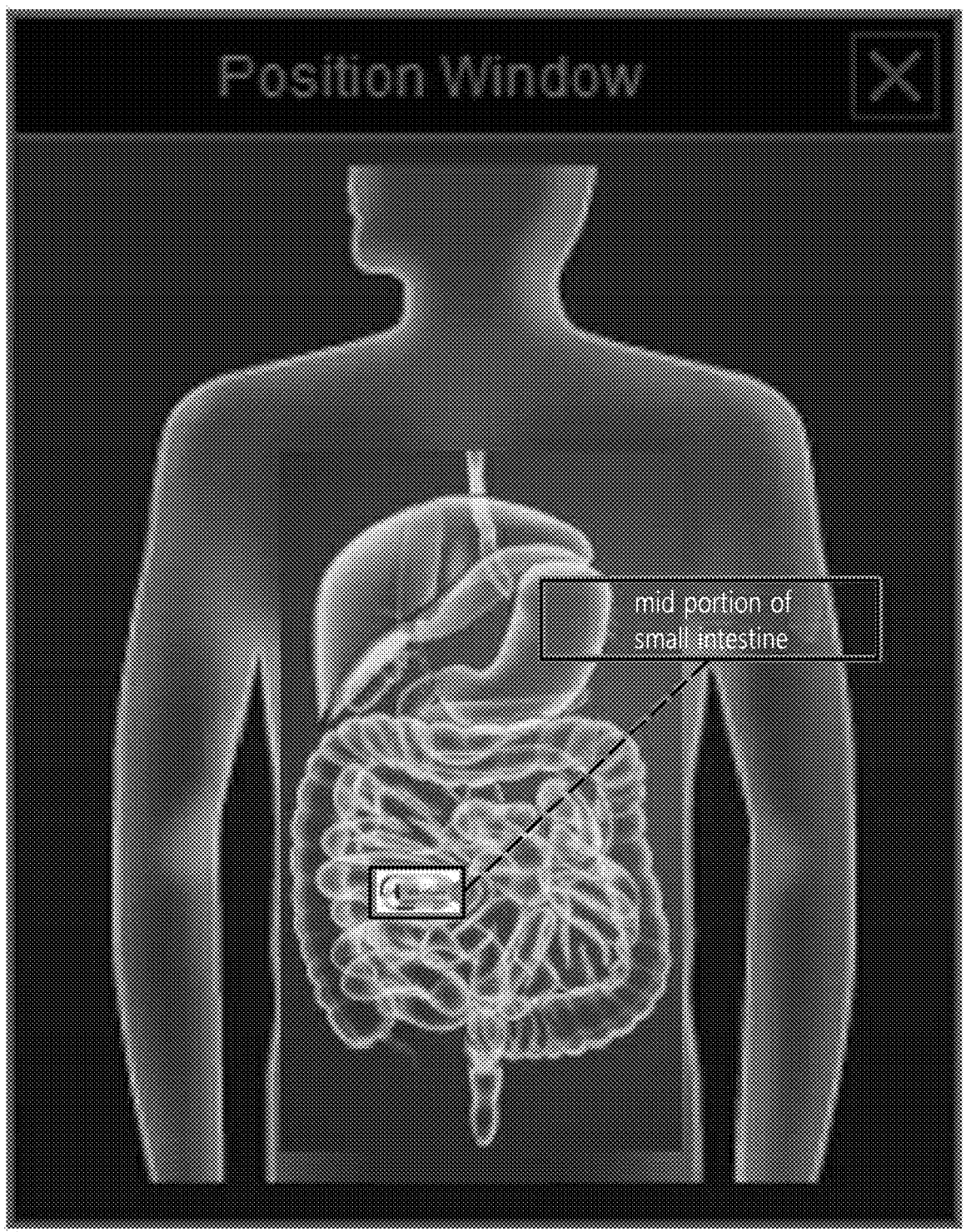
FIG. 7 schematically illustrates that an approximate location of a capsule endoscope in a body of a patient or a person to be examined is figured out based on a landmark function on a user interface or a display in the organ classification system according to an embodiment of the disclosure.

FIG. 7 schematically illustrates that an approximate location of a capsule endoscope in a body of a patient or a person to be examined is figured out based on a landmark function on a user interface or a display in the organ classification system according to an embodiment of the disclosure Conventionally, the location of the capsule endoscope in a body of a patient or a person to be examined has been displayed on the user interface based on a reception rate of human body communication. However, when the reception rate of human body communication is used to display the location of the capsule endoscope on the user interface, there is a problem that the location of the capsule endoscope is inaccurate. Therefore, as shown in FIG. 7, according to the disclosure, the time bar 160 is generated by classifying the organs in the input image based on the deep learning, and then the approximate location of the capsule endoscope is figured out based on the marking function of the landmark 170.

Specifically, unlike a dot conventionally displayed in the human body, the time-bar generator 150 according to the disclosure may indicate the location of the capsule endoscope in an organ model showing the inside of a certain human body in connection with the marking of the landmark 170. The landmark 170 is marked at a frame, in which an image corresponding to an organ starts to appear, in the time bar 160, and such a frame in which the image corresponding to the organ starts to appear is an image captured by the capsule endoscope at the corresponding frame. Therefore, when a user clicks the landmarks 170 with the input unit, the capsule endoscope is indicated in the organ model showing the inside of a certain human body as shown in FIG. 7 so that the user can easily figure out the location of the moving capsule endoscope.

In addition, the location of the capsule endoscope may be more specifically shown with respect to the landmarks of the organs. In other words, with respect to the landmarks of esophagus, stomach, small intestine and large intestine, the location of the capsule endoscope may be represented as an early portion, a mid portion and a late portion of esophagus; an early portion, a mid portion and a late portion of stomach; an early portion, a mid portion and a late portion of small intestine; and an early portion, a mid portion and a late portion of large intestine.

In this way, the organ classification system and method according to the disclosure are convenient. In the organ classification system and method according to the disclosure, the organ classification system may previously learn the organ images classified into the plurality of organs. Based on the learned organ images, the organ images input in real time are classified according to the organs, and the time bar of the organ image is generated and provided to a specialist, thereby providing convenience in reading a clinical case.

Further, it is possible to save time. In the organ classification system and method according to the disclosure, the organ classification system may previously learn the organ images classified into the plurality of organs, and use the binary search technique to raise the searching speed of the organ images in the future. Therefore, it is possible to save time in classifying the organ images acquired in real time.

The foregoing embodiments of the disclosure are described for illustrative purpose only, and various modifications, changes and additions can be made without departing from the spirit and scope of the disclosure by a person having ordinary knowledge in the art and fall within the scope of the appended claims.

The invention claimed is:

1. A system for classifying types of organs, the organ classification system comprising:
    a searcher configured to search for a frame, in which an image corresponding to an organ starts to appear, in an input image based on a plurality of organ images previously learned according to types of organs;
    an acquirer configured to acquire an image of the found frame in the input image; and
    a storage configured to store location information about the found frame in the input image,
    wherein the searcher is configured to use a binary search method to search for the frame, in which the image corresponding to the organ starts to appear, in the input image,
    wherein the input image comprises a first organ image, a second organ image, a third organ image and a fourth organ image;
    the first organ image corresponds to esophagus, the second organ image corresponds to stomach, the third organ image corresponds to small intestine, and the fourth organ image corresponds to large intestine; and
    the first organ image, the second organ image, the third organ image and the fourth organ image are input in sequence from the first organ image to the fourth organ image.

2. The organ classification system of claim 1, wherein the searcher is configured to perform a binary search with regard to the input image based on the binary search method, identify whether the found organ image is further upstream or downstream than a target organ image, and continue the binary search for searching for the frame, in which the target organ image starts to appear, in an upstream or downstream direction.

3. The organ classification system of claim 1, wherein
in a case where the searcher searches for a frame, in which the second organ image starts to appear, based on the binary search method,
the binary search is continued when the found organ image is identified as the second organ image, the third organ image or the fourth organ image after the binary search is first performed with regard to the input image; and
the binary search is terminated and sequential searching is performed when the found organ image is identified as the first organ image.

4. The organ classification system of claim 1, wherein
in a case where the searcher searches for a frame, in which the third organ image starts to appear, based on the binary search method,
the binary search is continued when the found organ image is identified as the third organ image or the fourth organ image after the binary search is first performed with regard to the input image; and
the binary search is terminated and sequential searching is performed when the found organ image is identified as the first organ image or the second organ image.

5. The organ classification system of claim 1, further comprising a landmark display configured to display a landmark corresponding to the frame, in which the image corresponding to the organ starts to appear, based on the location information about the found frame, in the input image.

6. The organ classification system of claim 5, further comprising a time-bar generator configured to generate a time bar based on information about display of the landmark and display the time bar on a user interface.

7. The organ classification system of claim 6, wherein the time bar represents esophagus, stomach, small intestine and large intestine in sequence.

8. The organ classification system of claim 6, wherein the time-bar generator is configured to display the time bar with a plurality of sections, of which lengths are relatively varied depending on the number of frames in images corresponding to esophagus, stomach, small intestine and large intestine.

9. The organ classification system of claim 6, wherein an image corresponding to an organ is displayed on the user interface when a user moves an input unit to the landmark.

10. The organ classification system of claim 6, wherein the time-bar generator is configured to generate the time bar in which esophagus, stomach, small intestine and large intestine are represented with different colors.

11. An organ classification method comprising:
by a searcher, searching for a frame, in which an image corresponding to an organ starts to appear, in an input image based on a plurality of organ images previously learned according to types of organs;
by an acquirer, acquiring an image of the found frame in the input image; and
by a storage, storing location information about the found frame in the input image,
wherein the searcher is configured to use a binary search method to search for the frame, in which the image corresponding to the organ starts to appear, in the input image,
wherein the input image comprises a first organ image, a second organ image, a third organ image and a fourth organ image;
the first organ image corresponds to esophagus, the second organ image corresponds to stomach, the third organ image corresponds to small intestine, and the fourth organ image corresponds to large intestine; and
the first organ image, the second organ image, the third organ image and the fourth organ image are input in sequence from the first organ image to the fourth organ image.

* * * * *